US008464574B2

(12) United States Patent
Smida et al.

(10) Patent No.: US 8,464,574 B2
(45) Date of Patent: *Jun. 18, 2013

(54) HYDROSTATIC TESTING TOOL AND METHODS OF USE

(75) Inventors: Charles R. Smida, Isanti, MN (US); Darrell E. Morse, Rochester, MN (US); Daniel L. Lozinski, Coon Rapids, MN (US)

(73) Assignee: Airmo, Inc., Minneapolis, MN (US)

(*) Notice: Subject to any disclaimer, the term of this patent is extended or adjusted under 35 U.S.C. 154(b) by 56 days.

This patent is subject to a terminal disclaimer.

(21) Appl. No.: 13/096,704

(22) Filed: Apr. 28, 2011

(65) Prior Publication Data

US 2011/0210522 A1   Sep. 1, 2011

Related U.S. Application Data

(63) Continuation of application No. 12/027,138, filed on Feb. 6, 2008, now Pat. No. 7,934,415.

(60) Provisional application No. 60/888,624, filed on Feb. 7, 2007.

(51) Int. Cl.
*G01M 3/32* (2006.01)
*G01N 3/12* (2006.01)

(52) U.S. Cl.
USPC .................................. 73/37; 73/40; 73/49.2

(58) Field of Classification Search
USPC ................................ 73/37, 40, 49.2, 52, 438
See application file for complete search history.

(56) References Cited

U.S. PATENT DOCUMENTS

| 4,528,840 | A | 7/1985 | Wass |
| 4,834,137 | A | 5/1989 | Kawaguchi et al. |
| 5,548,992 | A | 8/1996 | Hallett et al. |
| 6,694,802 | B1 | 2/2004 | Comardo |
| 6,981,404 | B2 | 1/2006 | Johns et al. |
| 7,934,415 | B2 * | 5/2011 | Smida et al. .................. 73/37 |

FOREIGN PATENT DOCUMENTS

| DE | 3935636 | 5/1991 |
| JP | 62-73135 | 4/1987 |

* cited by examiner

*Primary Examiner* — Daniel Larkin
(74) *Attorney, Agent, or Firm* — Moore & Hansen, PLLC

(57) ABSTRACT

A hydrostatic testing tool for testing containers, hoses or the like under high pressures. The testing tool having a coupling that threadably engages a threaded aperture of a test container without having to be rotated into the threaded aperture. The hydrostatic testing tool may be hooked up to a source of pressurized medium and the tool includes a container-engaging head having a plurality of collet segments that each have a threaded surface that can expand radially outward, partially due to the force of the pressurized medium, to engage a threaded aperture of the test container, allowing for the formation of a liquid and/or gas tight seal under high pressures. The testing tool further includes an actuating unit connected to the head that controls the movement of the collet segments with a piston or the like.

15 Claims, 7 Drawing Sheets

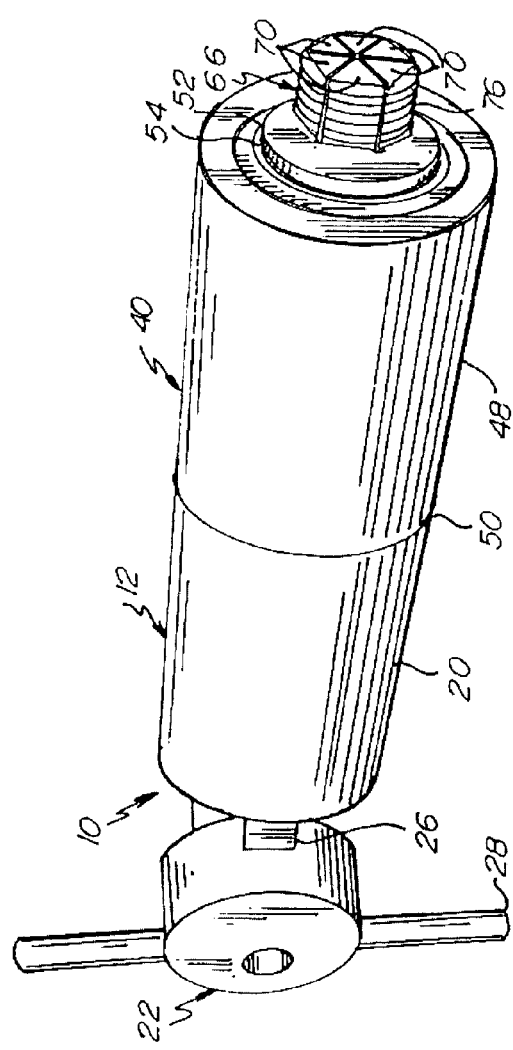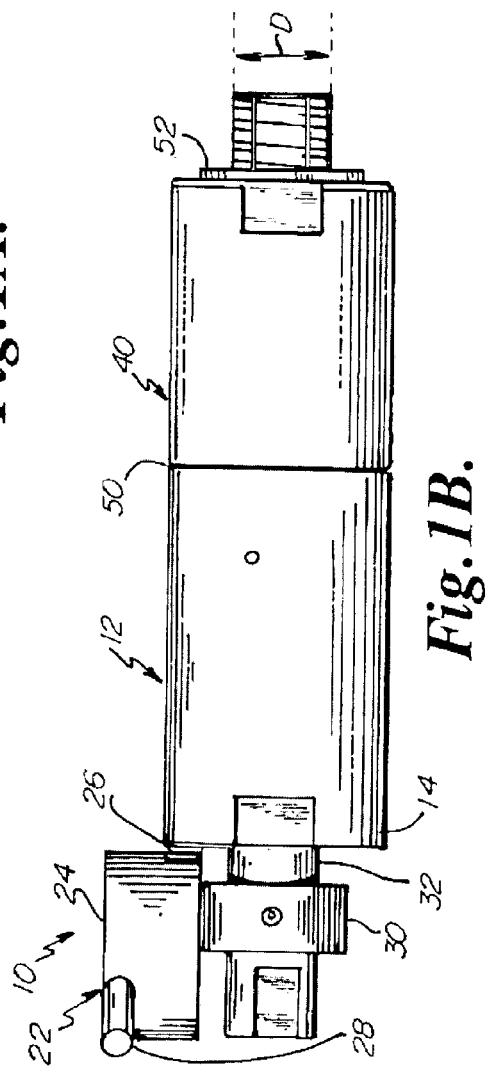

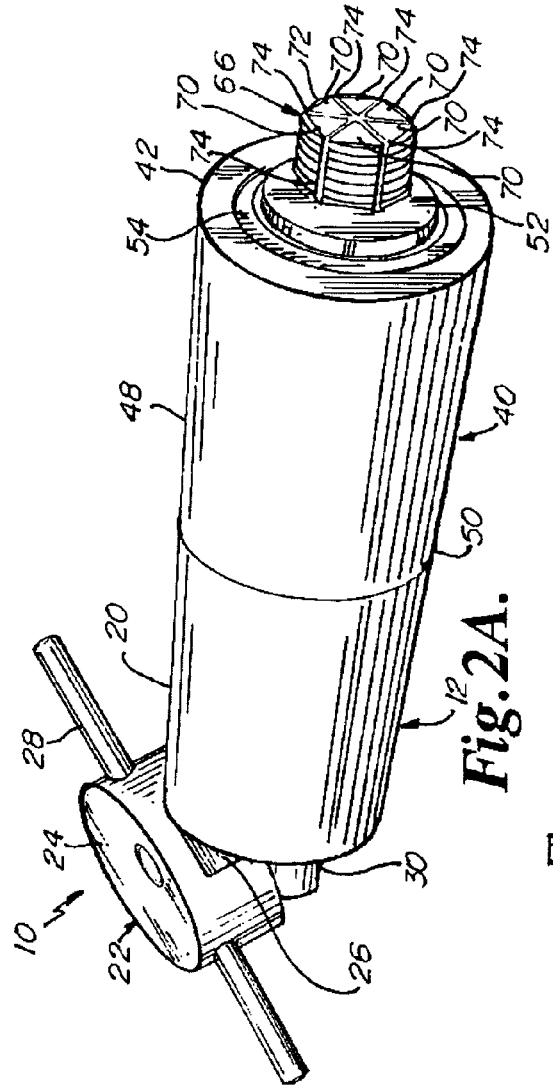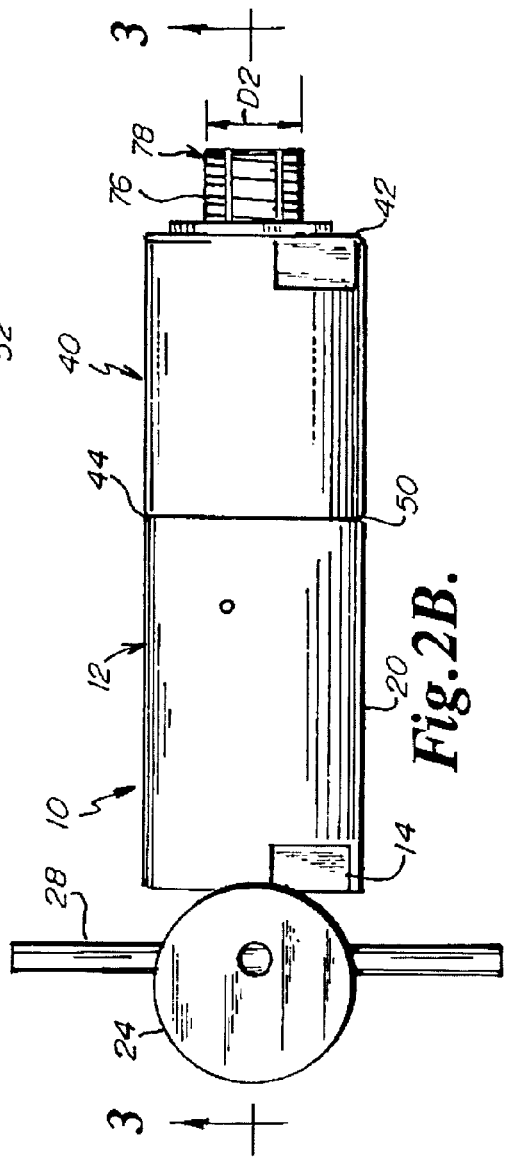

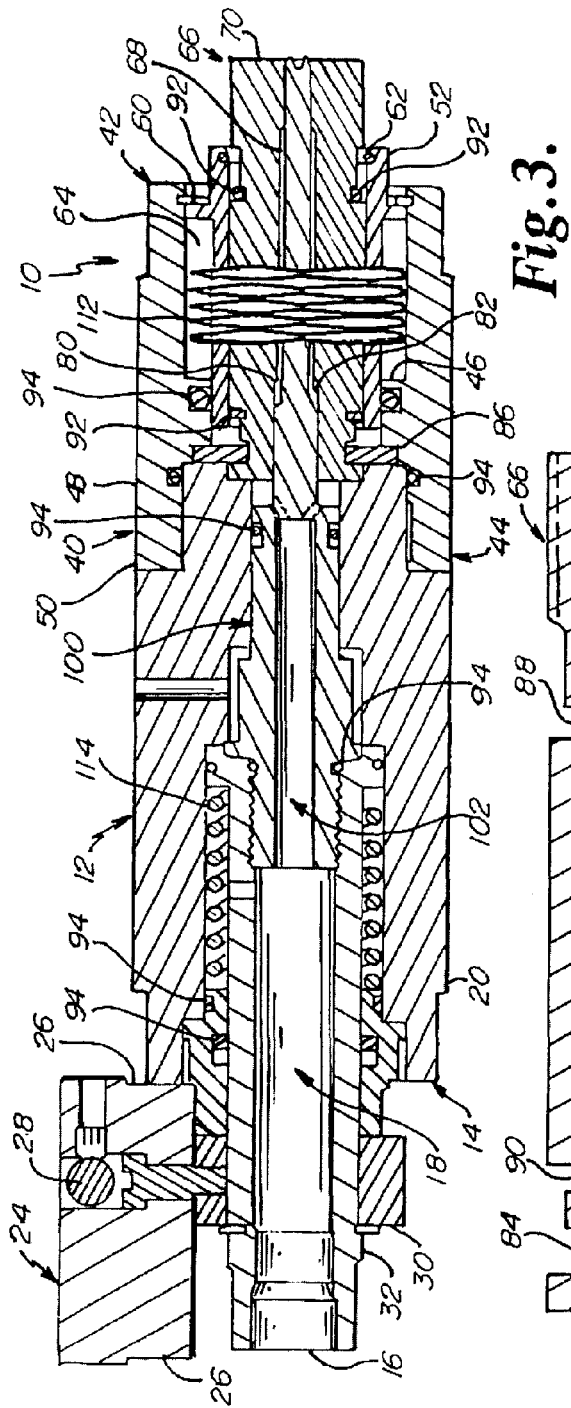
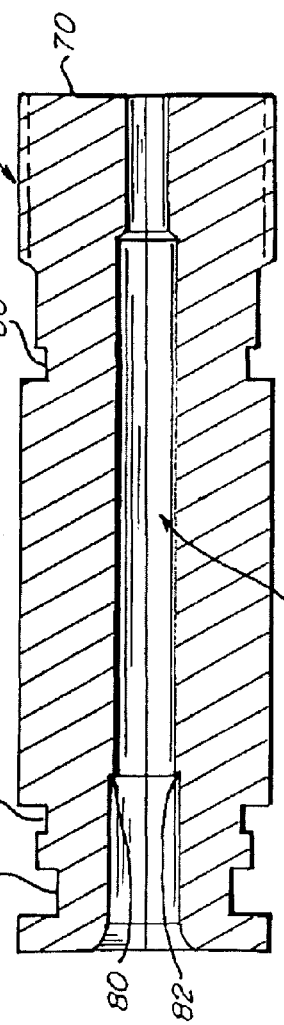
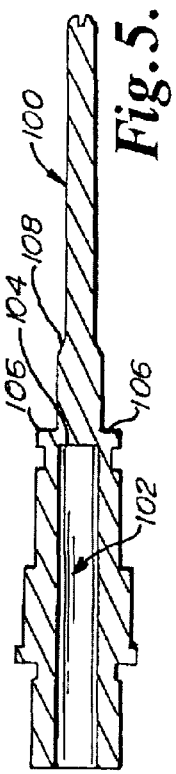
Fig. 3.
Fig. 4.
Fig. 5.

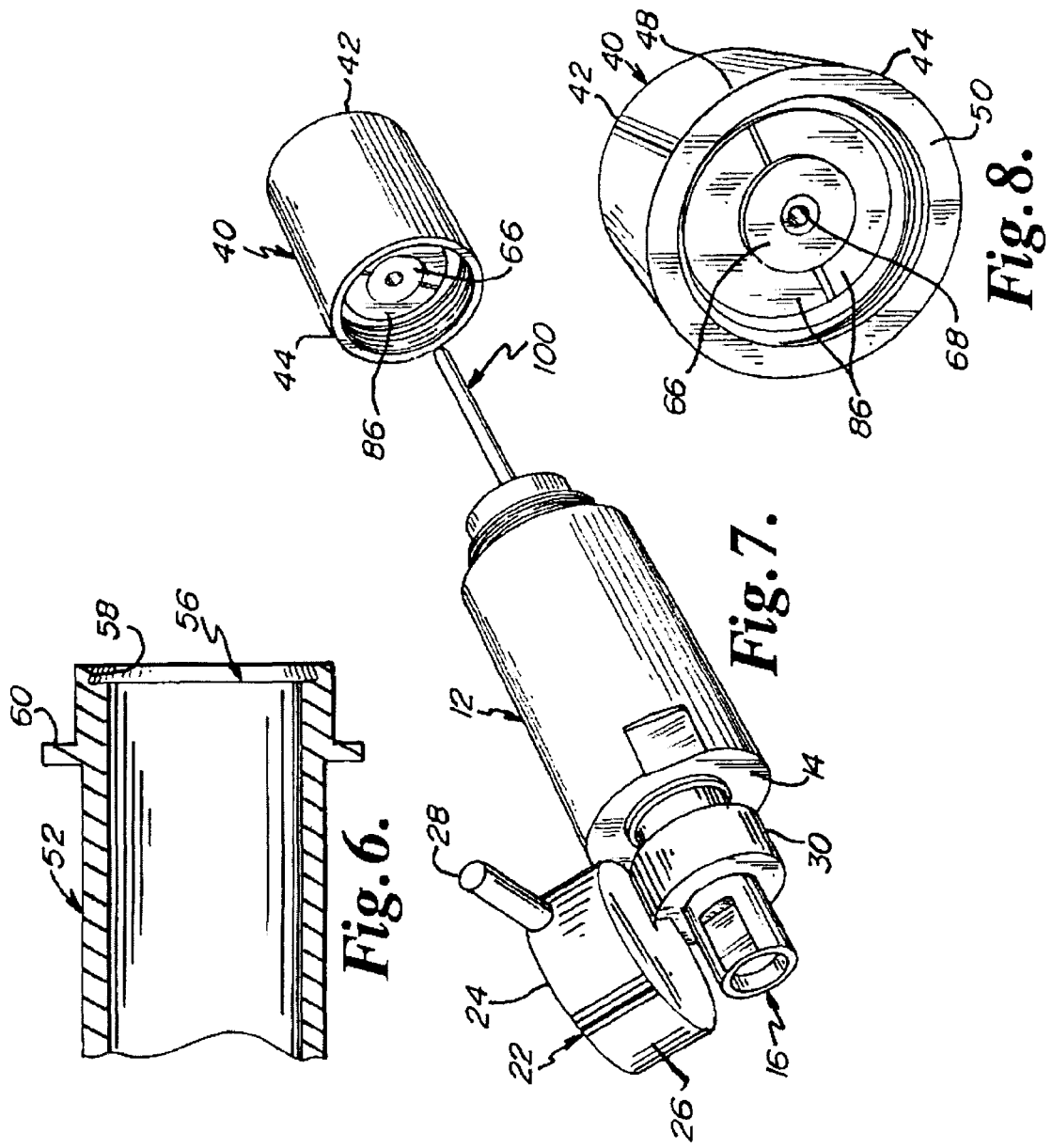

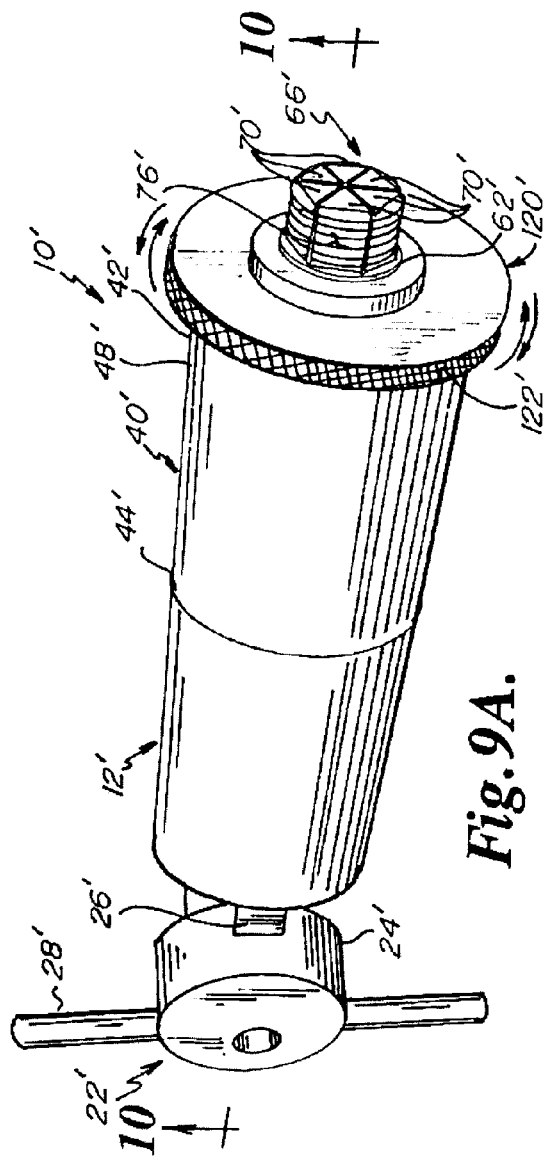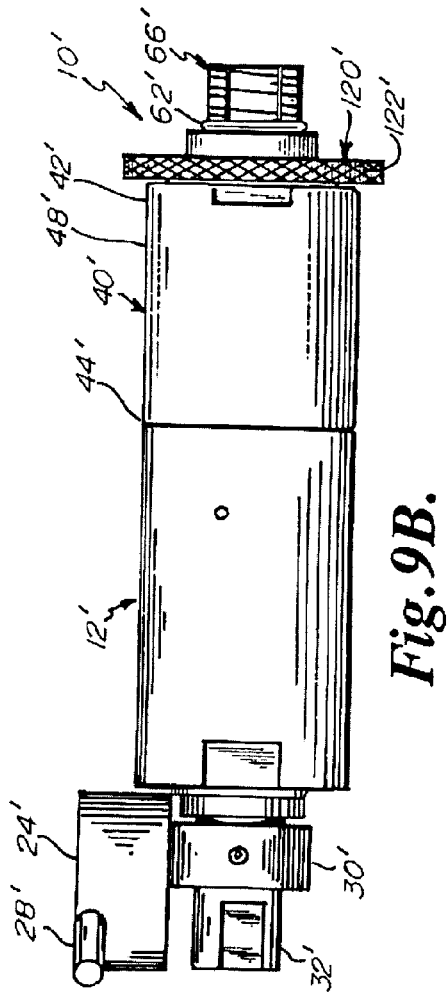

HYDROSTATIC TESTING TOOL AND METHODS OF USE

RELATED APPLICATION

The present application is a continuation of U.S. patent application Ser. No. 12/027,138, now U.S. Pat. No. 7,934,415, filed Feb. 6, 2008, which application claimed the benefit of U.S. Provisional Application No. 60/888,624, filed Feb. 7, 2007, both of which are herein incorporated by reference.

BACKGROUND OF THE INVENTION

1. Field of the Invention

The present invention relates generally to a hydrostatic testing tool. Particularly, the present invention relates to a hydrostatic testing tool having a coupling that threadably engages a threaded aperture of a test article without having to be rotated into the threaded aperture. More particularly, the present invention relates to a hydrostatic testing tool, which has a plurality of threaded collet segments that can expand radially outward to engage a threaded aperture of a test article to form a junction between the testing tool and the test article, which provides a liquid tight seal when the testing tool is operatively secured to the test article.

2. Description of the Related Art

Hydrostatic testing tools are used for testing the strength and integrity of test articles such as, metal bottles, containers, pressure carrying hoses and the like, wherein the bottle, container or hose generally has a filler/discharge aperture with an internal, threaded female coupling.

Typical containers to be tested must be able to safely contain gases and liquids stored at high pressures. The containers have various commercial applications but are often used, for example, in the medical equipment industry for storage of gases and gaseous liquids under high pressure. Typically, the containers will have an internal volume ranging between about 0.5 cubic feet to about 1.5 cubic feet. The containers are generally tested for strength using pressures of more or less than about 6000 pounds per square inch.

Each article to be tested will have an internal thread on its filler/discharge aperture. When these articles are tested, the test equipment is usually attached to the threaded aperture of the articles in one of two known ways. The first method is to rotate a threaded end of the testing tool into the threaded aperture of the article to produce a tight seal. This method generally requires complex automatic equipment to do the threading and unthreading needed to connect the tool to the large quantity of articles that are typically tested in a given time interval. This could be done by hand, but however it is done, it is extremely time consuming and limits the rate of test production.

The second known method is to insert an expandable rubber plug into the threaded aperture of the container and to then mechanically expand the rubber plug to sealably engage the threaded aperture. This method has not been shown to provide a reliable seal between the test article and testing tool.

The present invention addresses limitations and problems associated with the prior art.

SUMMARY OF THE INVENTION

The present invention provides a hydrostatic testing tool for testing a test article, such as a container, having a threaded aperture. The testing tool comprising an actuator unit and a head interconnected to the actuator unit. The head including a collet body having a plurality of collet segments collectively forming a cylindrical outer perimeter having a variable diameter, each collet segment having a threaded surface on the outer perimeter such that the actuator unit can selectively vary the diameter of the outer perimeter.

It is an object of the present invention to provide a hydrostatic testing tool that may be quickly secured and unsecured to a threaded aperture of a test article, such as a container, hose or the like. It is another object of the present invention to provide a hydrostatic testing tool that is durable, provides a reliable seal and cannot become dislodged from the threaded aperture during testing.

Preferred embodiments of the present invention achieve these and other objectives by providing a hydrostatic testing tool including a container-engaging head. The head preferably includes a generally cylindrical attachment body that is connected to an actuator unit having a central channel. The actuator unit preferably has a rear end where an inlet aperture can be sealably attached, in any known way, to a source of high-pressure fluid such as, gas, liquid or the like, preferably liquid, during testing. The pressurized fluid entering the inlet aperture preferably flows along the central channel toward the head of the tool.

The head of preferred embodiments further includes a longitudinally extending central chamber which communicates with the central channel of the actuator unit. The head of preferred embodiments additionally has a hollow cylindrical sleeve which is slidably received into, and contained within, the chamber. The sleeve is retained within the chamber by a retaining snap ring after being slid into the chamber from the front end of the head.

The head of preferred embodiments further includes an attachment body that houses a collet body of generally cylindrical configuration which is inserted into the chamber of the head from the rear end of the head before the head is threaded onto the actuator unit. The collet body of preferred embodiments includes a plurality of collet segments having a cylindrical outer perimeter. The collet segments of preferred embodiments are somewhat pie wedge shaped in cross section, moveable relative to each other and fit together to generally form a cylindrical shape. All of the collet segments, when properly aligned with each other, cooperate to define a generally continuous thread around the cylindrical outer perimeter that corresponds to or mates with the threaded aperture of the test article.

The collet body of preferred embodiments further includes an annular ring slot near its rearmost end. A removable two-piece split lock ring is slipped into the ring slot of preferred embodiments and helps lock the collet body in place relative to the attachment body. The front of the actuator unit of this embodiment bears against the two-piece lock ring when the actuator unit is connected to the head. In essence, the two-piece ring restricts (but does not wholly prevent) the collet body from moving forward, and the actuator unit restricts (but does not wholly prevent) the collet body and the lock ring from moving rearward. The ability of the collet segments to move forward and rearward, however slight, allows the collet segments to slightly adjust their longitudinal positions relative to one another to align with the threaded aperture. The collet body of this embodiment has an internal longitudinal channel extending rearwardly along its central axis from the front of the collet body and communicating with the actuator unit channel. A sliding piston, which is retained and selectively controlled by the actuator unit, can move forward and rearward along the central axis of the channel to radially expand the collet segments outwardly to engage the threaded aperture. In preferred embodiments, the testing tool further includes a sleeve or knurled knob, such that when the knob is rotated, the seal between the testing tool and the test article is enhanced.

The piston of this embodiment includes an internal piston channel extending from its rear end and communicating with the central channel. The piston channel ends midway along the piston where two smaller piston ports extend forwardly and outward to the outer periphery of the piston to allow pressurized fluid material, such as gas or liquid, to flow from the piston channel and along the piston ports to reach the collet segments.

Referring again to the channel formed along a central longitudinal axis of the collet body of this embodiment, the sliding piston is positioned within the channel for forward and rearward movement along the central axis of the collet body. As the piston moves forward, an annular shoulder of the piston contacts shoulders of the collet segments and pushes the collet segments radially outward from the central axis from an initial rest or unexpanded position to an expanded position, causing the diameter of the cylindrical outer perimeter of the threaded collet segments to increase uniformly along the collet body length so that the threaded collet segments strongly, mateably and evenly engage the threaded aperture so as to reliably seal the junction between the testing tool and the test article and retain the test article during high pressure testing.

The collet body of preferred embodiments additionally has front and rear annular slots each retaining a biasing device, such as a stretchable O-ring, snap ring or the like, that applies a force to urge the collet segments radially inward and together so as to retain and return the collet segments to an initial, unexpanded position. When the collet segments of preferred embodiment are in the unexpanded position, the cylindrical outer perimeter diameter is small enough to allow the collet segments to slide longitudinally within the threaded aperture of the container. When the collet segments are in a radially expanded position, the diameter of the cylindrical outer perimeter is increased to closely match, tightly engage and retain the threaded aperture.

When the collet segments of the preferred embodiment are in a radially expanded position, there is a gap created between each collet segment that reduces the risk of the fluid material flow path becoming obstructed and allows pressurized fluid material, preferably liquid, to flow through the gaps to enter into the test article.

The biasing devices of preferred embodiments allow the separate collet segments to move forwardly or rearwardly, slightly and independently of each other so as to permit the respective threaded surfaces to independently self-align with the threaded aperture and to more readily engage the threaded aperture when portions of the threaded aperture are somewhat irregular or damaged.

A wave spring is positioned within the central chamber preferred embodiments and extends between a rear shoulder of the head and an outwardly extending annular sleeve flange on the sleeve to spring bias the sleeve forwardly toward and against the retaining snap ring. At the front end of the sleeve is a sleeve slot in which a sealing O-ring resides in preferred embodiments. The wave spring and the sealing O-ring devices play an important role in creating an effective seal between the front end of the testing tool and the container or other test article.

When a container or other test article is to be tested, the collet segments of preferred embodiments are placed in an unexpanded position. The unexpanded collet segments can then be inserted into the threaded aperture of the container. As the testing tool is pressed against the container, the sleeve is pushed rearwardly by the container against the wave spring of preferred embodiments so as to cause the wave spring to bias the sleeve against the container. At this time, the actuator unit is activated to force the piston forward and into the collet body, causing the collet segments to move radially outward to an expanded position and solidly, threadably engage the threaded aperture of the container. Because the wave spring is now forcing the sleeve against the container, the sleeve O-ring in the front slot becomes compressed. At the contact circle between the container and the sleeve, the O-ring in the front slot is compressed between the container, the sleeve and the collet body to form a tight seal.

Preferably, the annular front slot has an angled front wall that slants rearwardly to better retain the O-ring and prevent it from escaping from the front slot during the forward and rearward movement of the sleeve relative to the O-ring. When the pressure is applied to the testing tool of preferred embodiments, the pressure also cooperates with the wave spring, sleeve and the container to force the O-ring against the container and further improve the seal therebetween.

The testing tool and methods of preferred embodiments of the present invention are much faster and easier to use than known methods that employ rotating a threaded end of the testing tool into the threaded aperture of the test article to produce a tight seal. Although that prior method works, it is time consuming to have to thread and unthread the testing tool from the threaded aperture and, assuming it is not done by hand, which would be really slow, it also requires complex automatic equipment to do the threading and unthreading needed to connect the tool to the large quantity of test articles that are typically tested in a given time interval.

The testing tool and methods of the present invention are also much safer and more reliable than the known expandable rubber plug method that involves inserting a rubber plug into the threaded aperture of the container and to then mechanically expanding the plug to sealably engage the threaded aperture. This known rubber plug method, when used at high pressures, has been unreliable and has created safety problems in that as the rubber plug wears, the container can sometimes slip off the rubber plug. When it does slip off, the container may be "launched" at high speed from the plug as the high pressure fluid within the container under test is released, resulting in a flying container that can endanger anyone or anything in its path.

These and various other advantages and features of novelty which characterize the present invention are pointed out with particularity in the claims annexed hereto and forming a part hereof. However, for a better understanding of the invention, its advantages and objects obtained by its use, reference should be made to the drawings of preferred embodiments of the present invention, which form a further part hereof, and to the accompanying descriptive matter, in which there is illustrated and described preferred embodiments of the present invention.

BRIEF DESCRIPTION OF THE DRAWINGS

In the drawings, in which corresponding reference numerals and letters indicate corresponding parts of the various embodiments throughout the several views, and in which the various embodiments generally differ only in the manner described and/or shown, but otherwise include corresponding parts;

FIG. 1A is a perspective view of a preferred hydrostatic testing tool 10 of the present invention in an unexpanded position;

FIG. 1B is a side view of the testing tool 10 of FIG. 1A;

FIG. 2A is a perspective view, similar to that of FIG. 1A, of the testing tool 10 of FIGS. 1A-1B, illustrating the testing tool in an expanded position;

FIG. 2B is a side view of the testing tool 10 shown in FIG. 2A;

FIG. 3 is a partial, cross-sectional view of the testing tool 10 as viewed along line 3-3 of FIG. 2B, illustrating the interior components of the testing tool including an actuator unit 12 having a central channel 18 that is interconnected to a head 40 having a collet body 66 with a channel 68 that is surrounded by a sleeve 52; and a piston 100 operatively connected within the actuator or central channel 18 and the collet channel 68 but showing the entire wave spring 112 as it would be seen from line 3-3 and not showing threaded fittings of the embodiment illustrated in FIG. 1A;

FIG. 4 is an expanded cross-sectional view of the collet body 66 of FIG. 3 illustrating the collet channel 68;

FIG. 5 is an expanded cross-sectional view of the piston 100 of FIG. 3;

FIG. 6 is an expanded cross-sectional view of the sleeve 52 of FIG. 3;

FIG. 7 is a partially exploded, perspective view of the testing tool 10 of FIGS. 1A-1B illustrating the actuator unit 12 and a container-engaging head 40;

FIG. 8 is an end view of a rear end 44 of the container-engaging head 40 of FIG. 7;

FIG. 9A is a perspective view of a preferred alternate hydrostatic testing tool 10' in an expanded position;

FIG. 9B is side view of the testing tool 10' of FIG. 9A;

DETAILED DESCRIPTION OF THE PREFERRED EMBODIMENTS

Figure 10:
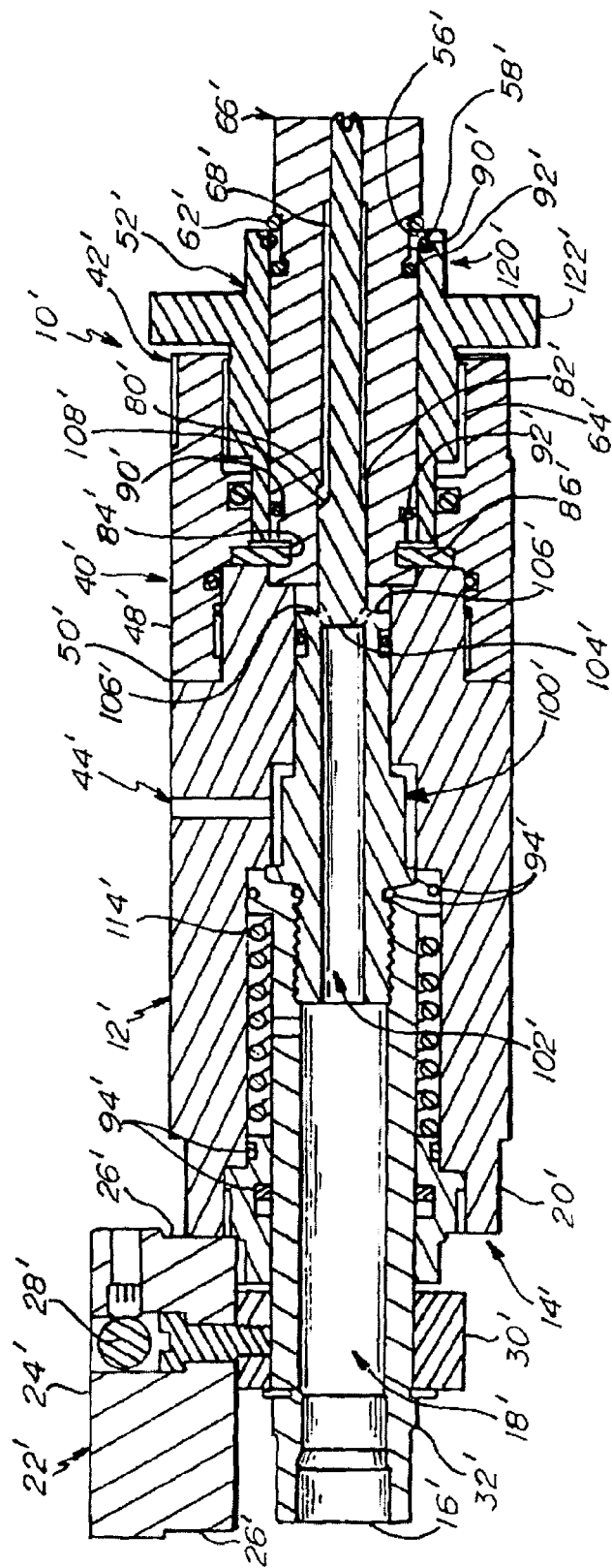
FIG. 10 is a cross-sectional view of the testing tool 10' as viewed along line 10-10 of FIG. 9B.

Preferred embodiments of the present invention are illustrated in FIGS. 1-12B. Referring in particular now to FIGS. 1-3 and 7-8, one embodiment of a hydrostatic testing tool 10 includes an actuator unit 12 interconnected to an article or container-engaging head 40. The head 40 is a generally cylindrical structure that includes a front end 42, a rear end 44 and an attachment body 48 which threads onto the actuator unit 12 at junction 50. The actuator unit 12 has a rear end 14 and at the rear end 14 is an inlet aperture 16 that is sealably attached in any known way to a source of high-pressurized fluid material (not shown), preferably liquid, for testing. It should be understood that although the inlet aperture 16 is described as for receiving liquid, the testing tool 10 of the present invention will work with gases as well. The pressurized liquid entering inlet aperture 16 flows along a central channel 18 in a direction towards the head 40. It will be appreciated that the container engaging head can engage test articles other than containers and the present invention is not, therefore, limited to use with any particular test articles.

Referring in particular now to FIGS. 1A and 3-5, the head 40, further has a longitudinally extending central chamber 68 that communicates with the channel 18 of the actuator unit 12. The head 40 also includes a hollow cylindrical sleeve 52, which is slidably received into and contained within the chamber 64. The sleeve 52 is preferably retained within the chamber 64 by a retaining, snap ring 54 or the like, after the sleeve 52 is slid into the chamber 64 from the front end 42 of the head 40.

The head 40 further includes a generally cylindrical collet body 66 that is inserted into the chamber 68 from the rear end 44 of the head 40 before the head is connected, preferably threadably attached, to the actuator unit 12. The preferred collet body 66 has a plurality of collet segments 70 and an annular ring slot 84 near its rear end. A removable two-piece split lock ring 86 is slipped into the ring slot 84 and helps lock the collet body 66 in place relative to the attachment body 48. The actuator unit 12 bears against the two-piece split lock ring 86 when the actuator unit 12 is connected to the head 40. In essence, the split lock ring 86 restricts (but does not wholly prevent) the collet body 66 from moving forward, and the actuator unit 12 restricts (but does not wholly prevent) the collet body 66 and the split lock ring 86 from moving rearward. Such forward and rearward movement, however slight, allows the collet segments 70 to slightly adjust their longitudinal positions relative to one another. The collet body 66 has an internal longitudinal chamber 68 extending rearwardly along its central axis from the front of the collet body 66 and communicates with the actuator unit channel 18. A sliding piston 100, which is retained and selectively controlled by the actuator unit 12, moves forward and rearward along the central axis of the collet channel 68 to radially expand the collet body 66 inward and outward, as is described in more detail below.

The piston 100 has an internal piston channel 102 extending from its rear end and communicating with the central channel 18. The channel 102 ends midway along the piston 100 at the channel end 104 where two smaller piston ports 106 extend forwardly and outward to the outer periphery of the piston 100 to allow pressurized liquid to flow from the channel 102 and along the ports 106 to reach the collet body 66. A spring 114 maintains contact between the actuator assembly 22 and the rear body 14 for extending and retracting of the piston 100 from the collet body 66. Extending the piston 100 causes the collet body 66 to expand and grip the threaded aperture T of a test article or container C, while retracting the piston 100 allows the collet body 66 to constrict and release its grip on the threaded aperture T.

The preferred collet body 66 has six collet segments 70, which are somewhat pie wedge shaped in cross-section, moveable relative to each other and which fit together to from a cylindrical outer perimeter 72 having a diameter "D". Each of the collet segments 70 has a threaded surface 76 around the cylindrical outer perimeter 72 near its front end 78 and the threaded surface 76 corresponds to a threaded surface defining the threaded aperture T of the test container C (see also, FIG. 11). All of the collet segments 70, when properly aligned with each other, cooperate to define a generally continuous threaded surface 76 around the cylindrical outer perimeter 72 of the collet segments 70, which corresponds to the threaded aperture T of the test container C. The generally continuous threaded surface 76 is separated by the area between the respective collet segments 70.

Referring again to the channel 68 formed along the central longitudinal axis of the collet body 66, the sliding piston 100 is positioned within the channel 68 and the chamber 64 for forward and rearward movement along the central axis of the collet body 66. Referring now also to FIGS. 3-6, as the piston 100 moves forward, an annular shoulder 108 of the piston 100 contacts shoulders 80 and 82, respectively on the collet segments 70 (see, FIG. 4) and pushes the collet segments 70 radially outward from the central axis from an initial rest or unexpanded position (see FIG. 1B) to an expanded position (see FIG. 2B), causing the unexpanded diameter "D" of the cylindrical outer perimeter 72 to increase uniformly to a second diameter "D2" so that the threaded collet segments 70 strongly, mateably and evenly engages the threaded aperture T so as to reliably retain the container C on the testing tool 10 during high pressure testing.

The preferred actuator unit 12 is illustrated in FIGS. 1-3. FIGS. 1A and 1B show the preferred actuator unit 12 further including a body 20 interconnected to an actuator assembly 22 having a generally cylindrical portion 24 and a lever 28 extending laterally through the generally cylindrical portion 24. Preferably, the generally cylindrical portion 24 is interconnected, off-center, to a collar 30 circumscribing a shaft 32 that is operatively connected to the piston 100. The preferred generally cylindrical portion 24 includes a recess 26 such that when the lever 28 is rotated, the generally cylindrical portion 24 correspondingly rotates. As shown in FIGS. 1A and 1B, when the generally cylindrical portion 24 is rotated far enough such that the body 20 enters the recess 26, the collar 30 and the shaft 32, are pushed rearwardly, thus moving the piston 100 (see FIG. 3) rearwardly as well and placing the collet segments 70 in the unexpanded position. As shown in FIGS. 2A and 2B, when the lever 28 is further rotated as to forcedly position the body 20 outside of the recess 26, the collar 30 and the shaft 32, and thus the piston 100, slide forward and the collet segments 70 move into the engaged position. In preferred embodiments, the generally cylindrical portion 24 will include two recesses 26 approximately 180 degrees from each other so that generally cylindrical portion 24 requires less rotation to un-expand the collet segments 70. It is noted that this is simply the preferred actuator unit and that any other known plunging device can be used to control the movement of the piston. It will be understood that the actuating unit can be actuated either mechanically or pneumatically.

The collet body 66 is preferably, first formed as an integral, cylindrical stainless steel unit, and the threaded surface 76 is then cut into the outer perimeter 72 near the front end 78 of the collet body 66 so as to correspond to the threaded aperture T. The central channel 68 is then bored longitudinally through the collet body 66 along the central axis, and the shoulders 80 and 82 may be machined within the collet body 66 during the boring operations. At this stage, the collet body 66 is cut along three radial planes into the six collet segments 70, or, alternatively, as many or as few radial planes as needed to create the desired number of collet segments. It should be noted that the threaded surface 76 on each collet segment 70 is likely to be different in alignment from the other collet segments, and, therefore, the segments are preferably aligned in the same order as that which existed before cutting in order that the threaded surfaces as a whole retains its original nature on the collet body.

As best shown in FIGS. 3-4, the preferred collet body 66 has front and rear annular slots 88, 90 extending about its outer periphery and a biasing device 92, such as a stretchable O-ring, snap ring or the like is received into each of the front and rear slots 88, 90 to apply a force to urge the collet segments 70 radially inward and together so as to retain and return the collet segments 70 to an initial unexpanded position. When the collet segments 70 are in the unexpanded position, the cylindrical outer perimeter 72 should have a diameter "D" small enough to allow the threaded surfaces 76 to slide longitudinally within the threaded aperture T of the container C (see also, FIG. 11). When the collet segments 70 are in a radially expanded position, the original diameter "D" of the cylindrical outer perimeter 72 is increased to the second diameter "D2'" that closely matches, tightly engages and retains the threaded aperture T. When the collet segments 70 are in a radially expanded position, there is a gap 74 created between each collet segment 70 (See FIG. 2A) that reduces the risk of the fluid material or liquid flow path becoming obstructed and allows pressurized liquid to flow through the gaps 74 and enter into the container C.

The use of the biasing devices 92 in the front and rear slots 88, 90 of the collet body 66 allows the separate segments 70 of the collet body 66 to move forwardly or rearwardly, slightly and independently of each other so as to have their respective threaded surfaces 76 be more self-aligning with the threaded aperture T and even to more readily engage the threaded aperture when the threaded aperture may be somewhat irregular or damaged. The preferred biasing device 92 is an O-ring made of BUNA (nitrile), but the preferred material may vary depending on the substance to be pressurized as will be determinable by one of ordinary skill in the art in light of this disclosure. It will be appreciated that O-rings made of other suitable materials may also be used.

Referring now also to FIGS. 3-6, a wave spring 112 is positioned within the chamber 64 of the head 40 and extends between a rear shoulder 46 of the head 40 and an outwardly extending annular sleeve flange 60 of the sleeve 52 to spring bias the sleeve 52 forwardly toward and against the retaining ring 54. At the front end of the sleeve 52 is a sleeve slot 56, which preferably contains a sealing O-ring 62 or the like. The slot 56 cross-section is best shown in FIG. 6. The wave spring 112 and the O-ring 62 in the sleeve slot 56 play an important role in creating an effective seal between the front end of the tool 10 and the container and are best understood in conjunction with the following description of how the tool engages and seals the container.

When a container C is to be tested, the collet segments 70 are placed in their unexpanded positions so that the collet segments fit within the threaded aperture T of the test container aperture C. The unexpanded collet segments 70 are slidably inserted into the threaded aperture of the container. As the tool 10 is pressed against the container, the sleeve 52 is pushed rearwardly by the container against the wave spring 112 so as to cause the wave spring to bias the sleeve 52 against the container. At this time the actuator unit 12 is activated to force the piston 100 forward and into the collet body 66, causing the collet segments 70 to move radially outward to expanded position and solidly, threadably engage the threaded aperture of the container. This results in the container being fixed relative to and "locked on" to the collet body 66. Because the wave spring 112 is forcing the sleeve 52 against the container, the O-ring 62 in the sleeve slot 56 becomes compressed. At the contact circle between the container and the sleeve 52, the O-ring 62 is compressed between the container, the sleeve 52 and the collet body 66 to form a tight seal.

As best shown in FIG. 6, the sleeve slot 56 has an angled front wall 58 that slants rearwardly to better retain the O-ring 62 and prevent the O-ring from escaping from the sleeve slot 56 during the forward and rearward movement of the sleeve 52 relative to the O-ring 62. When the pressure is applied to the tool 10, the pressure also cooperates with the wave spring 112, sleeve 52 and the container to force the O-ring 62 against the container and further improve the seal therebetween.

Referring again to FIG. 3, the preferred testing tool 10 further includes a plurality of O-rings 94 positioned throughout the actuator unit 12 and the head 40. These O-rings 94 function as seals for the actuation of the internal parts of the tool 10 and their placement and usage will be apparent to one of ordinary skill in the art in light of this disclosure.

FIGS. 9A-10 illustrate another embodiment of a hydrostatic testing tool 10' largely similar to the embodiment illustrated in FIGS. 1-8, which was subsequently developed and is believed to be preferred. The testing tool 10' includes an actuator unit 12' interconnected to a container-engaging head 40'. As in the previous embodiment, the head 40' is a generally cylindrical structure that includes a front end 42', a rear end 44' and an attachment body 48' which threads onto the actuator unit 12' at junction 50'. The actuator unit 12' has a rear end 14' and at the rear end 14' is an inlet aperture 16' that is sealably attached in any known way to a source of high-pressure fluid material such as liquid or gas for testing (see in particular, FIG. 10). The pressurized liquid or gas entering inlet aperture 16' flows along a central channel 18' in a direction towards the head 40'.

Referring in particular now to FIG. 10, the head 40', further has a longitudinally extending central chamber 68' which communicates with the channel 18' of the actuator unit 12'. The head 40' also includes a hollow cylindrical sleeve 52' which is slidably received into and contained within the chamber 64'. The sleeve 52' is preferably retained within the chamber 68'.

The head 40' further includes a generally cylindrical collet body 66' that is inserted into the chamber 68' from the rear end 44' of the head 40' before the head is connected, preferably threadably attaching, to the actuator unit 12'. The preferred collet body 66' has a plurality of collet segments 70' and an annular ring slot 84' near its rear end. A removable two-piece split lock ring 86' is slipped into the ring slot 84' and helps lock the collet body 66' in place relative to the attachment body 48'. The actuator unit 12' bears against the two-piece split lock ring 86' when the actuator unit 12' is connected to the head 40'. In essence, the split lock ring 86' restricts (but does not wholly prevent) the collet body 66' from moving forward, and the actuator unit 12' restricts (but does not wholly prevent) the collet body 66' and the split lock ring 86' from moving rearward. As with the previous embodiment, such forward and rearward movement, allows the collet segments 70' to slightly adjust their longitudinal positions relative to one another. The collet body 66' has an internal longitudinal chamber 68' extending rearwardly along its central axis from the front of the collet body 66' and communicates with the actuator unit channel 18'. A sliding piston 100', which is retained and selectively controlled by the actuator unit 12', moves forward and rearward along the central axis of the collet channel 68' to radially expand the collet body 66' inward and outward.

The piston 100' has an internal piston channel 102' extending from its rear end and communicating with the central channel 18'. The channel 102' ends midway along the piston 100' at the channel end 104' where two smaller piston ports 106' extend forwardly and outward to the outer periphery of the piston 100' to allow pressurized liquid to flow from the channel 102' and along the ports 106' to reach the collet body 66'. A spring 114' maintains contact between the actuator assembly 22' and the rear body 14' for extending and retracting of the piston 100' from the collet body 66'. Extending the piston 100' causes the collet body 66' to expand and grip the threaded aperture T of a test article or container C, while retracting the piston 100' allows the collet body 66' to constrict and release its grip on the threaded aperture T (see also, FIGS. 12A-12B).

As illustrated in FIG. 9A, the preferred collet body 66' has six collet segments 70', which are somewhat pie wedge shaped in cross-section, moveable relative to each other and which fit together to from a cylindrical outer perimeter 72'. Each of the collet segments 70' has a threaded surface 76' around the cylindrical outer perimeter 72' near its front end and the threaded surface 76' corresponds to a threaded surface defining the threaded aperture T of the test container C (see, FIG. 11). All of the collet segments 70', when properly aligned with each other, cooperate to define a generally continuous threaded surface 76' around the cylindrical outer perimeter 72' of the collet segments 70', which corresponds to the threaded aperture T of the test container C. The generally continuous threaded surface 76' is separated by the area between the respective collet segments 70'.

Referring again to the channel 68' formed along the central longitudinal axis of the collet body 66', the sliding piston 100' is positioned within the channel 68' and the chamber 64' for forward and rearward movement along the central axis of the collet body 66'. As the piston 100' moves forward, an annular shoulder 108' of the piston 100' contacts shoulders 80' and 82', respectively on the collet segments 70' and pushes the collet segments 70' radially outward from the central axis from an initial rest or unexpanded position (see also, FIG. 1A) to an expanded position (as illustrated in FIG. 9A), causing the unexpanded diameter of the cylindrical outer perimeter to increase uniformly to a second diameter so that the threaded collet segments 70' strongly, mateably and evenly engages the threaded aperture T so as to reliably retain the container C on the testing tool 10' during high pressure testing.

The preferred actuator unit includes a body 20' interconnected to an actuator assembly 22' having a generally cylindrical portion 24' and a lever 28' extending laterally through the generally cylindrical portion 24'. Preferably, the generally cylindrical portion 24' is interconnected, off-center, to a collar 30' circumscribing a shaft 32' that is operatively connected to the piston 100'. The preferred generally cylindrical portion 24' includes a recess 26' such that when the lever 28' is rotated, the generally cylindrical portion 24' correspondingly rotates. When the generally cylindrical portion 24' is rotated far enough such that the body 20' enters the recess 26', the collar 30' and the shaft 32', are pushed rearwardly, thus moving the piston 100' rearwardly as well and placing the collet segments 70' in the unexpanded position (see also, FIG. 1A). When the lever 28' is further rotated as to forcedly position the body 20' outside of the recess 26', the collar 30' and the shaft 32', and thus the piston 100', slide forward and the collet segments 70' move into the engaged position. In preferred embodiments, the generally cylindrical portion 24' will include two recesses 26' approximately 180 degrees from each other so that generally cylindrical portion 24' requires less rotation to unexpand the collet segments 70'. As with the previous embodiment, the actuator unit shown is simply the preferred actuator unit and that any other known plunging device may be used to control the movement of the piston. It will be understood that the actuating unit can be actuated either mechanically or pneumatically.

Figure 12B:
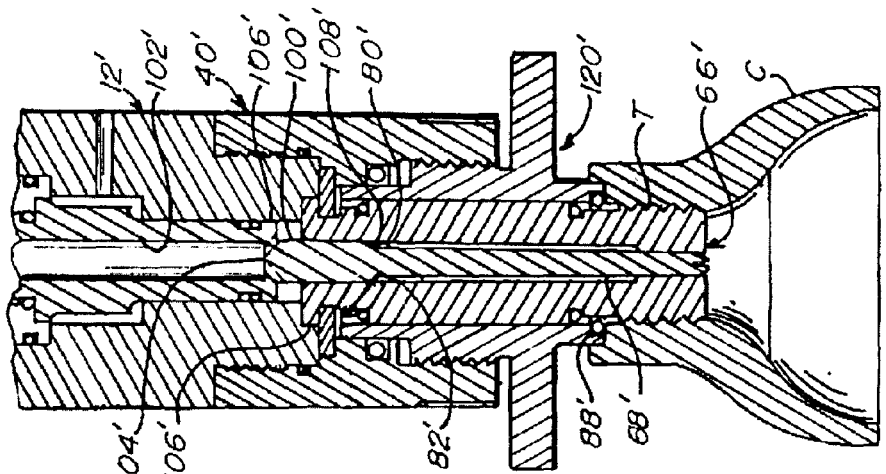
FIG. 12B is a cross sectional view of the testing tool 10' of FIGS. 11-12A, when the testing tool 10' is in the expanded position.
Figure 12A:
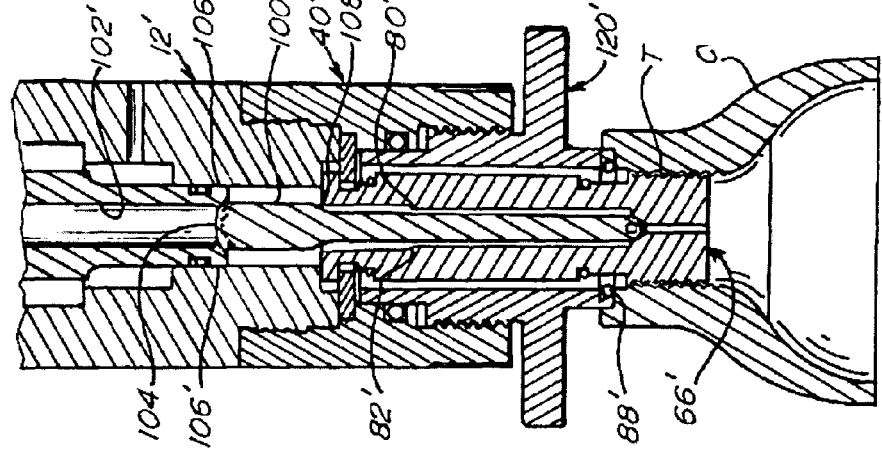
FIG. 12A is a cross-sectional view of the testing tool 10' of FIG. 11 as it is inserted into the threaded aperture T in the unexpanded position.
Figure 11:
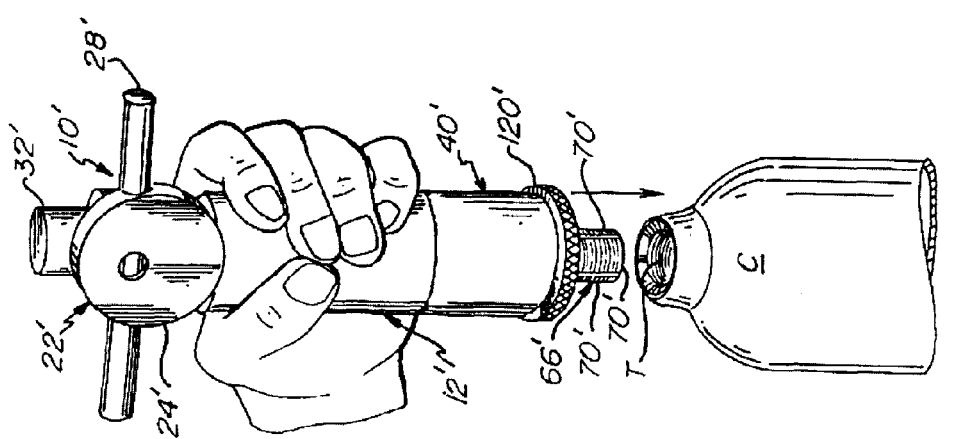
FIG. 11 is a perspective view of the testing tool 10' before insertion into a threaded aperture T of a container C that is to be tested.

Referring also to FIGS. 10, 12A, and 12B, similar to the previous embodiment, the preferred collet body 66' has front and rear annular slots 88', 90' extending about its outer periphery and a biasing device 92', such as a stretchable O-ring, snap ring or the like is received into each of the front and rear slots 88', 90' to apply a force to urge the collet segments 70' radially inward and together so as to retain and return the collet segments 70' to an initial unexpanded position. When the collet segments 70' are in the unexpanded position, the cylindrical outer perimeter 72' should have a diameter small enough to allow the threaded surfaces 76' to slide longitudinally within the threaded aperture T of the test article or container C. When the collet segments 70' are in a radially expanded position, the original diameter of the cylindrical outer perimeter 72' is increased to the second diameter that closely matches, tightly engages and retains the threaded aperture T of the container C (see, FIG. 12B). When the collet segments 70' are in a radially expanded position, there is a gap 74' created between each collet segment 70' (See FIG. 9A) that reduces the risk of the fluid material flow path becoming obstructed and allows pressurized fluid material to flow through the gaps 74' and enter into the container C.

The use of the biasing devices 92' in the front and rear slots 88', 90' of the collet body 66' allows the separate segments 70' of the collet body 66' to move forwardly or rearwardly, slightly and independently of each other so as to have their respective threaded surfaces 76' be more self-aligning with the threaded aperture T and even to more readily engage the threaded aperture when the threaded aperture is somewhat irregular or damaged.

In this preferred embodiment, the testing tool 10' further includes a knob 120'. The knob 120' preferably has a knurled surface 122' so that it is easy to grip and rotate. The knob 120' rotates relative to the front end 42' which has internal threads. When a user rotates the knob 120' in the clockwise direction relative to the right end view of the testing tool 10', the knob 120' will move away from end of the front end 42'. During use, the knob 120' is preferably only rotated clockwise after the collet body 66' is securely engaged with the threaded aperture T of the container C. By rotating the knob 120' clockwise it causes a face seal 62' retained in the knob 120' to be pressed against the container C resulting in compression of the face seal 62' to create a leak tight condition superior to that of the embodiment of FIGS. 1A-8. The force of compressing the face seal 62' is reacted by the collet body 66' gripping the threaded aperture T. After testing tool 10' usage where the collet segments 70' of the collet body 66' are released and not gripping the threaded aperture T, the knob 120', is rotated counterclockwise to reset the knob 120' for the next application.

To further increase the seal between the testing tool 10' and the container C, the sleeve slot 56' has an angled front wall 58' that slants rearwardly to better retain the face seal or O-ring 62' and prevent the O-ring from escaping from the sleeve slot 56' during the forward and rearward movement of the sleeve 52' relative to the O-ring 62'. As also discussed above, when the pressure is applied to the tool 10', the pressure also cooperates with the knob 120', cylindrical sleeve 52' and the container C to force the O-ring 62' against the container C and further improve the seal therebetween.

As with the embodiment of FIGS. 1A-8, the preferred testing tool 10' further includes a plurality of O-rings 94' or the like positioned throughout the actuator unit 12' and the head 40'. These O-rings 94' function as seals for the actuation of the internal parts of the tool 10' and their placement and usage will be apparent to one of ordinary skill in the art.

Although only a container is illustrated, it will be appreciated that the hydrostatic testing tool can be used to test other various test articles having a threaded aperture, such as a hose or the like.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A tool for engaging and retaining an article having a threaded aperture, the tool comprising:
    a head having a collet body including at least three collet segments collectively forming a cylindrical outer perimeter having a variable perimeter and a central longitudinal axis, each collet segment having a threaded surface; and
    an actuator unit interconnected with the head and constructed and arranged to selectively vary the diameter of the outer perimeter to selectively engage and disengage the threaded aperture of the article.

2. The tool of claim 1, wherein the actuator unit includes an actuator assembly having a lever; and
    the lever being movable to selectively vary the diameter of the outer perimeter.

3. The tool of claim 1, wherein the collet body further includes:
    an annular slot located rearward of the threaded surfaces and extending about the collet body outer perimeter; and
    a biasing device received into the annular slot to apply a force to urge the collet segments radially inward and together so as to bias the collet segments in an initial unexpanded condition.

4. The tool of claim 3, further comprising a sliding piston that is retained by the actuator unit and is selectively movable forwardly within the actuator unit and toward the head from an initial piston position and cooperating with the biasing device to move the collet segments to an expanded condition by overcoming the force of the biasing device and permitting the biasing device force to return the collet segments to an unexpanded condition when the piston moves rearwardly to the initial piston position.

5. The tool of claim 4, wherein the collet segments are moveable parallel to the longitudinal axis independently of each other to allow the segments to longitudinally, independently align their respective threaded surfaces with the threaded aperture of the article.

6. The tool of claim 1, further comprising a sliding piston that is retained by the actuator unit and is selectively movable forwardly within the actuator unit and toward the head from an initial piston position to thereby move the collet segments from an unexpanded condition to an expanded condition, the collet segments returning to the unexpanded condition when the piston moves rearwardly to the initial piston position.

7. The tool of claim 1, wherein the collet body includes six collet segments.

8. The tool of claim 1, wherein the collet segments are moveable parallel to the longitudinal axis independently of each other to allow the segments to longitudinally, independently align their threaded surfaces with the threaded aperture of the article.

9. A tool for engaging and retaining an article having a threaded aperture, the tool comprising:
    a head having a collet body and including a plurality of collet segments arranged around a central longitudinal axis, each collet segment having an outer surface, the outer surfaces of the plurality of collet segments collectively forming an outer perimeter constructed and arranged to enter and engage the threaded aperture, the collet segments being moveable toward and away from the central axis to cause the size of the outer perimeter to vary when the segments move toward and away from the central axis, each collet segment having a thread on at least part of its outer surface to match and engage the threaded aperture when the collet segments move outward from the central axis into contact with the threaded aperture; and
    an actuator unit interconnected with the head and constructed and arranged to selectively move the collet segments outward and inward relative to the central axis to vary the size of the outer perimeter to thereby selectively engage and disengage the threaded aperture of the article.

10. The tool of claim 9, wherein the actuator unit further includes an actuator assembly having a lever, wherein the lever can be moved to selectively expand the collet segments.

11. The tool of claim 9, further comprising:
a sleeve at least partially positioned within the head; and
a seal retained in the sleeve,
wherein rotating the sleeve causes the seal to be pressed against the article and results in compression of the seal to create a seal between the sleeve and the article.

12. The tool of claim 9, wherein
the collet body has an annular slot extending about its outer perimeter; and
a biasing device received into the annular slot to apply a force to urge the collet segments together so as to bias the collet segments in an unexpanded condition.

13. The tool of claim 12, further comprising a sliding piston that is retained by the actuator unit and is selectively movable forwardly within the actuator unit and toward the head from an initial piston position and cooperating with the biasing device to move the collet segments to an expanded condition by overcoming the force of the biasing device and permitting the biasing device force to return the collet segments to an unexpanded condition when the piston moves rearwardly to the initial piston position.

14. The tool of claim 9, further comprising a sliding piston that is retained by the actuator unit and moves forward and rearward within the actuator unit to selectively expand and contract the collet segments.

15. The tool of claim 9, wherein the collet body includes six collet segments.

* * * * *